United States Patent [19]
Dolan et al.

[11] Patent Number: 4,678,483
[45] Date of Patent: Jul. 7, 1987

[54] METHODS OF PARTICULATE MEASUREMENT

[75] Inventors: Michael J. Dolan, Laurel Springs; Timothy L. Hilbert, Clementon, both of N.J.; John D. Snyder, Pittsburgh, Pa.

[73] Assignee: Mobil Oil Corporation, New York, N.Y.

[21] Appl. No.: 336,010

[22] Filed: Dec. 30, 1981

[51] Int. Cl.[4] ............................................. G01N 33/00
[52] U.S. Cl. .......................................... 55/97; 55/270; 73/28; 73/863.23; 436/175; 436/177; 436/181; 436/908
[58] Field of Search ...................... 422/101; 23/232 R; 73/28, 863.23; 55/97, 270; 436/120, 174, 181, 908, 119, 175, 177

[56] References Cited

U.S. PATENT DOCUMENTS 3,838,972 10/1974 Richards et al. .................. 23/232 R
4,221,569  9/1980 Kebbekus ............................ 436/120
4,235,098 11/1980 Tisch ................................. 73/863.23

OTHER PUBLICATIONS

Sargent-Welch, Sargent-Welch Scientific Co., 1971, pp. 490-491.

Primary Examiner—Arnold Turk
Attorney, Agent, or Firm—A. J. McKillop; M. G. Gilman; L. P. Hobbes

[57] ABSTRACT

Method for measuring particulates in flue gas streams containing chemicals reactive with trace elements in the filters is disclosed which features pretreating the filters with chemicals comparable to those in the process stream whereby the reactions are completed prior to the measurement step, in particular, prior to establishment of the tare weight of said filter.

3 Claims, 2 Drawing Figures

METHODS OF PARTICULATE MEASUREMENT

FIELD OF THE INVENTION

This invention relates to the field of measurement of the quantity of particulate matter contained in a stack or flue gas stream. More particularly, the invention relates to improvements in the accuracy of methods presently used according to Environmental Protection Agency specifications to measure particulates in stack gas.

BACKGROUND OF THE INVENTION

As part of the continuing effort to improve the environmental quality, the Environmental Protection Agency has set certain standards for the quantity of particulates which can be emitted to the air from various industrial processes. The EPA has similarly specified the way in which compliance with their standards is to be measured. One such test for particulates is performed by weighing a filter paper of predetermined size, inserting it into a stack gas stream for a predetermined period and weighing it afterwards and calculating from the difference and the relative area of the filter and stack the total number of pounds of particulates emitted per hour. There are several difficulties with the EPA test as presently defined. One is that the stack gas stream typically contains materials such as $H_2SO_4$ which are gaseous $SO_3$ at higher temperatures, e.g., above about 400° F., but tend to react with water vapor and to condense as acid when the stack gas temperature is below the dew point, which varies between about 225° and 400° F. depending on the concentration. Present EPA tests specify the temperature of the stack gas at which the sample is to be taken as being well below the dew point. Hence, liquified $H_2SO_4$ tends to collect on the filter, interfering with measurements of the particulates, which are of different compositions. The test could therefore be improved as to accuracy by performing it in a region of the stack where the gases are well above the dew point, allowing the $SO_3$ gases to pass through the filter, and not interfering with the accuracy of the measurement.

A second difficulty in the measurement of particulates in stack gas streams is that the filters, even when of very high quality quartz or borosilicate glass fiber filter materials, contain certain metallic impurities which tend to react with some of the components of the gas stream. Hence, some chemical species which would otherwise pass through the filter instead are attracted to the filter for chemical reaction and are bound up, thus again increasing the weight of the filter to a value higher than that which it would have had had only particulates physically trapped in the mesh of the filter been captured.

OBJECTS OF THE INVENTION

It is therefore an object of the invention to provide an improved method of measuring the amount of particulates in a flue gas stream.

A further object of the invention is to provide a method whereby only particulates physically entrapped within the fibers of the filter are captured for weighing.

Still another object of the invention is to provide a method for avoiding the capture of non-particulate matter on filter papers by chemical action.

SUMMARY OF THE INVENTION

The above needs of the art and objects of the invention are satisfied by the present invention according to which filter papers used for capturing particulates in flue gas streams containing $SO_3$ ions and the like are pretreated prior to use, in particular prior to weighing to establish a tare weight, by treatment with e.g., sulfuric acid whereby the metallic elements present in the filter material are prereacted so that no free sites for reaction with chemical elements contained in the flue gas stream remain present.

BRIEF DESCRIPTION OF THE DRAWINGS

The invention will be better understood if reference is made to the accompanying drawings in which.

DESCRIPTION OF THE PREFERRED EMBODIMENTS

As noted above, the present invention relates to improved accuracy of measurement of particulates in flue gas streams. It will be appreciated that this invention will have applicability in many sorts of systems wherein a filter or other desirably inert structure tends to react with a substance which must be accurately measured. The broad concept of the invention, i.e., prereacting all possible impurities in the filter or other inert member to render it truly inert thus has wide utility. The present invention was made, however, in the course of developing better test methods for measurement of particulate emissions from catalyst recovery systems in oil refining operations and it is with respect to this application of the invention that its preferred embodiment will now be described.

Figure 1:
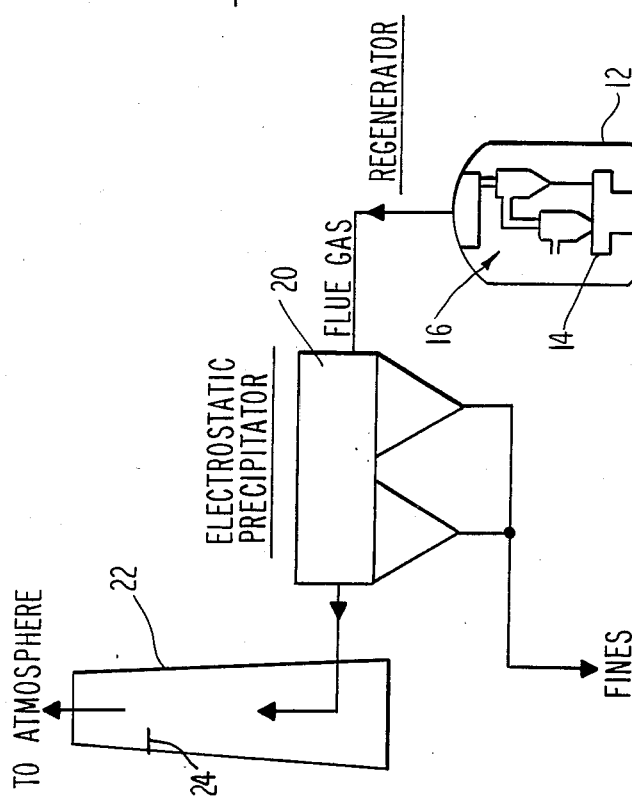
FIG. 1 shows an overall view of a system for refinement of crude oil comprising means for regeneration and recovery of catalysts used in the "cracking" of heavy hydrocarbons to lighter components in which the present invention plays an important part.

The broad overview of a petroleum refining plant is shown in FIG. 1. Gas is supplied to the base of the reactor unit 10, which is characterized as a fluidized catalytic cracking unit using zeolitic cracking catalysts. Such units are well-known and their details do not relate to the present invention. The cracked products are passed to a conventional main fractionating column 11 where they are separated into the various constituent parts as listed. The zeolitic catalysts used in cracking the gas are then regenerated in a regenerator 12. In the catalytic regenerator 12, coke is burned off the talcum powder-like catalyst in order to rejuvenate the catalyst. There are three devices which prevent the emission of the catalyst particles entrained in the hot exhaust system to the atmosphere. These devices are an inertial separator 14, a two-stage cyclone system indicated generally at 16 and an electrostatic precipitator 20. The coked catalyst particles enter the regenerator 12 in a combustion section. In this section the coke-laden catalyst is contacted concurrently with air supplied at the bottom of the regenerator, and the coke is burned to $CO_2$, $CO$ and $H_2O$. The mixture of the now rejuvenated catalytic particles in the flue gas leaves the combustor section at about 4 ft/sec. Without control apparatus, this total amount of catalyst particles in the size range between zero and 100 microns would enter the atmosphere as particulates. The amount of potential emissions has been calculated for data collected in a particular example of such a system on Apr. 21, 1981; on that day, the total potential particulate emissions were 2,711,449 lbs/hr.

The flue gas plus entrained particles travel up the regenerator at a velocity of about 2.5 ft/sec to the next control apparatus, the two-stage cyclone separator system 16. The mixture is accelerated to approximately 70 ft/sec as it enters the first stage of cyclone separation. Heavier particles are thrown to the wall by means of centrifugal force and after disengagment from the flue gas, fall by gravity down to the regenerator bed. The finer particles plus the flue gas pass out the top of the cyclone and into the second stage cyclone separator. Here smaller particles are similarly disengaged. At this point, the flue gas stream contains approximately 200 lbs/hr. of catalyst fines. The two-stage cyclone separator 16 has an overall efficiency of 99.95%, with the first stage 99.0% efficient and the second stage 98.5% efficient. The flue gas plus particles next enters the electrostatic precipitator 20. Here the particles are charged in an electric field and are attracted to an oppositely charged electrode where they are held until they are dislodged by mechanically "rapping" the cells. The gas stream leaving the electrostatic precipitator 20 contains 6 lbs/hr. of solid particulate matter. The individual efficiency of the electrostatic precipitator is thus 97%. The overall efficiency of the system including the inertial separator, the two-stage cyclone system and the electrostatic precipitator is 99.9998% reducing the potential particulate emissions of some 2,700,000 lbs/hr. to 6 lbs/hr. actual emissions.

Figure 2:
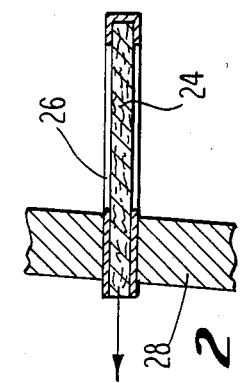
FIG. 2 is a schematic drawing showing the manner in which the filter may be conveniently inserted into and removed from the flue gas stack.

It is this last figure of 6 lbs/hr which must be met by the stack gas output from the refinery. Clearly accuracy of measurement is very important in a system where the overall efficiency need vary only slightly to greatly change the results of the test. In the presently defined EPA test, a filter of a corrosion and heat resistant material such as quartz, titanium or borosilicate glass fiber, perhaps with a paper backing is exposed to the flue gas in the stack 22. A schematic diagram of how this might be accomplished is shown in FIG. 2. The filter 24 is carried within a typically circular holder 26, which is inserted through an orifice in the wall 28 of the stack 22. The filter paper may be 5.5 cm in diameter when used with a 7½ ft. diameter stack. Typically 40 cu. ft. of stack gas will pass through the filter in about an hour, out of roughly 70,000 total cu. ft. released. A suitable filter is sold by the Whatman Ltd. Company of England under Model No. 934-AH. Other EPA-approved methods will more typically be used; for example, the filter can be carried in a box external to the stack, as well understood by those skilled in the art. Suitable equipment for the purpose is sold by Joy Manufacturing Co., under the trade name "Emission Parameter Analyzer". However, as discussed above, even a high quality filter paper contains some metallic impurities which can react with chemicals in the stack gas which would otherwise pass therethrough, thus adding an erroneous additional weight to the filter which will show up in the weighing of the filter and provide a misleading result to the testing. Table 1 below shows typical filter papers of the quartz, titania and borosilicate types analyzed for the presence of metals which can form sulfates with, e.g., $SO_3$ in the stack gas stream.

TABLE 1

Compositions of Filter Papers
(Only Extractable Metals Which Can Form Sulfates)

| Metal | Quartz | Titania | Borosilicate |
| --- | --- | --- | --- |
| Aluminum | 0.24% | 5.5% | 2.5% |
| Barium | 0.016% | 0.063% | 0.023% |
| Calcium | 0.35% | 8.5% | 4.0% |
| Potassium | 0.068% | .04% | 0.5% |
| Magnesium | 0.13% | 1.6% | 1.5% |
| Sodium | 0.7% | 1.0% | 9.0% |
| Zinc | 0.012% | 0.024% | 0.0045% |

As discussed above, the present inventors have found that in order that the trace metals present in the filter paper are prevented from reacting with the $SO_3/H_2SO_4$ in the flue gas, it is desirable to pretreat the papers thus tying up the alkaline sites and trace metals in the paper and reducing its reactability to $SO_3/H_2SO_4$ so as to give more accurate stack testing results. In particular, simply exposing the filter papers to sulfuric acid for a period of on the order of an hour by soaking them, is sufficient to prereact these alkaline sites and trace metals. When the paper is thereafter dried, weighed to establish a tare weight, exposed to the flue gas, dried to eliminate any water and condensed $H_2SO_4$, and reweighed to establish an amount of particulates collected, the difference figure will not include any chemically bonded elements found in the flue gas. In particular, metal sulfates and their many hydrates ($MSO_4 . nH_2O$) will no longer be formed during the testing process.

It will be appreciated, of course, by those skilled in the art that the broad concept of the invention is to prereact the alkali metals and trace elements, and that it would not be necessary to use the same chemicals present in the process stream for prereaction; any other chemical which would prereact with the same components of the filter could be used thus rendering the filter chemically inert.

While a preferred embodiment of the invention has been described, it should be appreciated that the method of the invention has broader applicability than that specifically described. In particular, the method of pretreating filters comprising trace elements which are reactive with components of a process stream can be applied to process streams not containing sulfates but containing other sorts of materials which would otherwise be bound up chemically to the filter papers, thus rendering the filtration operation more accurate. Moreover, of course, the invention has applicability to chemical processes far different from hydrocarbon refining operations as described above. Therefore, the above description of the invention should not be considered as a limitation on its scope, but merely as exemplary thereof; the scope of the invention is more properly defined by the following claims.

We claim:

1. A method of pretreating a filter of a corrosion- and heat-resistant material used to collect particulates from a process stream comprising $SO_3/H_2SO_4$, said filter comprising substances which react chemically with components of said process stream, comprising the step of:
   pretreating the filter by exposure to $H_2SO_4$ prior to exposure to said process stream, whereby said reactions take place prior to exposure of the filter to the process stream.

2. The method of claim 1 wherein said filter is weighed to establish a tare weight after said pretreatment step.

3. The method of claim 1 wherein said corrosion- and heat-resistant materials are selected from the group consisting of quartz, titanium and borosilicate glass fiber.

* * * * *